(12) United States Patent
Maindron

(10) Patent No.: US 6,337,079 B1
(45) Date of Patent: Jan. 8, 2002

(54) PRODUCT FOR PREVENTING THE PRESENCE OF AND/OR FOR DESTROYING TERMITES AND ITS PROCESS OF IMPLANTATION

(76) Inventor: Georges Maindron, 72, rue Mendes France, 44240 La Chapelle sur Erdre (FR)

( * ) Notice: Subject to any disclaimer, the term of this patent is extended or adjusted under 35 U.S.C. 154(b) by 0 days.

(21) Appl. No.: 09/358,698

(22) Filed: Jul. 21, 1999

(30) Foreign Application Priority Data

Jul. 21, 1998 (FR) .......................................... 98 09265

(51) Int. Cl.[7] .............................................. A01N 25/24
(52) U.S. Cl. ...................... 424/408; 424/405; 424/406; 424/409; 424/411; 424/419; 424/DIG. 11
(58) Field of Search ........................ 424/DIG. 11, 405, 424/406, 408, 409, 411, 419, 84; 514/120, 519, 531, 743

(56) References Cited

U.S. PATENT DOCUMENTS

| 4,166,111 A | * | 8/1979 | Cardarelli ..................... 424/78 |
| 4,237,114 A | * | 12/1980 | Cardarelli ..................... 424/78 |
| 4,400,374 A | | 8/1983 | Cardarelli |
| 4,900,551 A | * | 2/1990 | Ohtoubo et al. ............. 424/408 |
| 4,971,796 A | * | 11/1990 | Sjogren ....................... 424/417 |
| 5,567,429 A | * | 10/1996 | Senbo ......................... 424/405 |
| 5,856,271 A | * | 1/1999 | Cataldo et al. ............. 504/116 |
| 5,925,368 A | * | 7/1999 | Voris et al. .................. 424/405 |
| 6,001,382 A | * | 12/1999 | Leny ........................... 424/405 |
| 6,093,789 A | * | 7/2000 | Galinis et al. ................ 424/84 |
| 6,099,850 A | * | 8/2000 | Voris et al. .................. 424/411 |

FOREIGN PATENT DOCUMENTS

| GB | 2 276 171 | 9/1994 |
| WO | WO 95/18532 | 7/1995 |
| WO | WO 95/22902 | 8/1995 |
| WO | WO 97/37543 | 10/1997 |

* cited by examiner

Primary Examiner—Neil S. Levy
(74) Attorney, Agent, or Firm—Young & Thompson

(57) ABSTRACT

The invention relates to a termicidal product to prevent the presence of and/or to destroy termites in a suitable surrounding medium.

This product is characterized in that it has the form of an elongated solid body constituted a) of an extruded core constituting a solid degradable macroscopic matrix based on at least a polymeric binder and a substance active against termites, b) of an envelope of the core containing at least one substance active against termites, this active substance of the envelope being releasable in the surrounding medium, at least under the influence of moisture in the surrounding medium, such that, when the product is exposed to the surrounding medium, the quantity of active material freed per unit time within the surrounding medium by the envelope decreases with time.

13 Claims, 1 Drawing Sheet

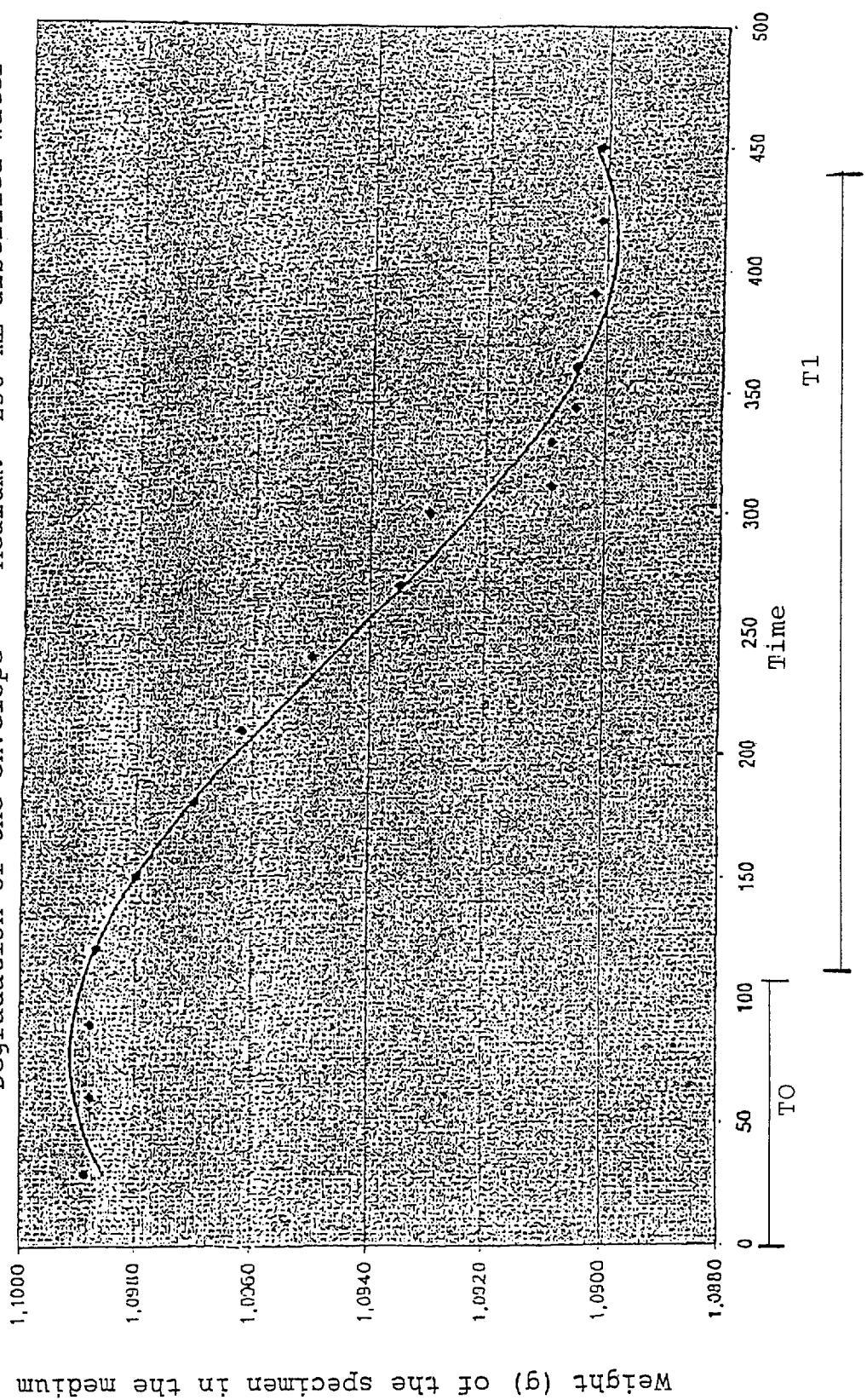

PRODUCT FOR PREVENTING THE PRESENCE OF AND/OR FOR DESTROYING TERMITES AND ITS PROCESS OF IMPLANTATION

The present invention relates to a product to prevent the presence of and/or to destroy termites as well as a process for implantation of this same product.

The propagation of termites nowadays requires preventive treatment of constructions, particularly buildings. This preventive treatment is carried out by the formation of horizontal and vertical barriers at the base of walls and in the walls themselves of the constructions. These barriers are nowadays produced by injection in the soil and in the walls, of an aqueous dispersion of a powerful insecticide powder.

The use of an aqueous dispersion has major drawbacks. Thus, it is known that the effective life of the treatment is not very long in the soil because, after treatment, the powder is easily entrained in rainwater. The effectiveness of the treatment is thus reduced. Moreover, the entrainment of the insecticide at a point distant from the site to be treated can give rise to subsoil pollution, in particular in the case of the presence of a phreatic layer. As a result, any overdosage which could be envisaged to improve the effective life of the treatment must be precluded. Moreover, the implantation of an aqueous dispersion in places with variable absorption properties, arising for example from the nature of the materials delimiting the emplacement, does not permit precise dosage of the truly active quantity of insecticide. Finally, the absence of controlled release of the active substance in the liquid state requires, for effectiveness over several years, the use of large quantities of active substance.

Compositions permitting controlled release of an insecticide have however been conceived. Such is the case of the composition described in U.S. Pat. No. 4,400,374. This floating composition, because destined for aquatic media, comprises a polymer, an active substance and a porogenic agent adapted to create a porous network within the polymeric matrix to permit water of the surrounding medium to come into contact with the active substance freed from the polymer. The kinetics of slow and progressive release thus obtained do not permit application of this composition for curative purposes. Moreover, the presence of the porogenic agent requires an environment with a high water content to be effective.

Other compositions are known, based on a polymer and an insecticide for various applications such as the protection of cables (GB-A-2.276.171) or of wood base material (WO97/37543). These compositions again do not permit preventive and curative treatment against termites.

A first object of the invention is to provide a product to destroy termites, whose design permits preventive and curative treatment against termites with a reduced initial quantity of active substance.

Another object of the present invention is to provide a product for destroying termites, whose design permits limiting the loss of the active substance in the ground or in the walls of the construction to be protected, and to reduce the quantity of active substance initially introduced into the product whilst preserving a high effectiveness of treatment over a long period of time.

Another object of the present invention is to provide a product to destroy termites, whose design permits on the one hand limiting the risk to the environment, in particularly by avoiding migration of the active substance through the phreatic layer by leaching, on the other hand to enclose totally the construction or the region to be protected.

Another object of the present invention is to provide a product to destroy termites, whose design permits easier handling and storage.

To this end, the invention has for its object a termicidal product to prevent in a prolonged manner the presence and/or to destroy termites, in a suitable environmental medium by placing the product into contact with said medium, said product containing at least one active substance to destroy termites, characterized in that it has the form of a generally elongated solid body constituted a) of a core in the form of an extrusion or molding or sinter and constituting a solid macroscopic matrix which degrades under the influence of the environmental medium, generally by biodegradation and/or biodispersion and/or solubilization and/or chemical or physical degradation, this core being based on at least one binding polymer preferably extrudable and at least one substance active against termites releasable into the environmental medium over a period of time T2.

b) an envelope about the core, containing at least one substance active against termites, this active substance of the envelope being releasable, into the environmental medium, at least under the influence of moisture of the environmental medium and/or a liquid introduced into said medium, according to a release profile such that, when the product is exposed to an environmental medium with a substantially constant moisture content near than 100%, the quantity of active material released per unit time into the environmental medium by the envelope decreases in the course of time over a predeterminable period of time T1, after an induction period T0, this time period T1 corresponding at most to T2 to give rise by means of the envelope to an initial rapid release of the active substance for a curative effect against termites and by means of the core a slow and prolonged release of the active substance for preventive effect against termites.

The inventors have determined that it is necessary to release over a short time a large quantity of active substance to obtain the curative effect then, to obtain preventive effect against a reinfestation by termites, to release slowly over a longer period of time a quantity of active substance so as to maintain in the environmental medium a quantity of active substance greater than or equal to the lethal dose. This curative effect is caused by the envelope of which at least one portion of the constituents soluble in water or in any liquid, permit the release over a short time of a large quantity of the active substance. Conversely, the preventive effect is performed by the core in which the polymer present slows the physical, chemical and/or enzymatic degradation of the core such that the release of the active substance can extend over a period at least equal to two years, the active substance of a core coming progressively to replace in the environmental medium the active substance released by the envelope. This design moreover permits reducing the quantity of active substance initially present in the product. Finally, the release of the active substance, relying essentially initially on the moisture of the environmental medium and thereafter on the moisture augmented by other parameters, such as the presence of microorganisms, the pH, the temperature . . . , is guaranteed. This release of the active substance can take place by slow dissolution, by diffusion and/or by erosion. Moreover, as termites grow essentially in moist media, the design of the product is perfectly adapted to these latter.

Finally, thanks to the preparation of the product in the form of a solid product, the quantity of active substance delivered is carried out in a sure manner, the risk of migration of the product into rainwater are reduced and the implantation of the product is facilitated.

The invention also has for its object a process for the implantation of a product for destroying termites in any location of a site to be protected, characterized in that it consists, in any order, on the one hand of carrying out an application of liquid, such as water, to or in the vicinity of the emplacement destined to receive the product according to the above definition, on the other hand in positioning said product in said emplacement.

The invention will be better understood from a reading of the description with embodiments and the single figure which represents the kinetic of liberation of the active substance contained in the envelope in suitable environmental medium.

The product to destroy termites, called a termicide, which is the object of the invention, comprises at least one active substance for the destruction of termites. This active substance must satisfy a certain number of criteria. This active substance must in particular be stable at temperatures of production of the product, remain stable and active within the normal pH range that is found in constructions or in the soil, and, of course, have the ability to destroy termites. The active substance used in the product is preferably selected from the group of substances formed by BENDIOCARB (trade mark) made by NOR-AM CHEMICAL Co., ISOFENPHOS (trade mark) made by MOBAY CHEMICAL Co., FENVALERATE (trade mark) made by ROUSSEL BIO Corporation, phenyl-pyrazole compounds, in particular FIPRONIL (trademark) made by Rhone-Poulenc responding to the molecular formula $C_{12}H_4Cl_2F_6N_4OS$, organochlorine compounds, such as ENDOSULFAN (trademark) made by ROUSSEL BIO Corporation, synthetic pyrethrinoide compounds, in particular BIFENTHRINE (trademark) made by FMC CHEMICAL Co., CYPERMETHRINE (trademark) made by ICI CHEMICAL Co. and FMC CHEMICAL Co., DELTAMETHRINE™, ALPHAMETRINE™, organophosphorus compounds such as CHLORPYRIFOS (trademark) made by DOW ELANCO and the pyrrol compounds such as CHLORFENAPYR (trademark) made by Cyanamid Agro.

As mentioned above, the product to destroy termites, which is the object of the invention, is constituted by a core and an envelope which each contain a substance active against termites, these actives substances of the envelope and of the core being of identical or different nature.

The core is obtained by shaping generally by extrusion, molding or sintering of at least one polymer binder, preferably extrudable, and a substance active against termites to form a solid macroscopic matrix giving to the product a mechanical strength sufficient to permit ultimately the implantation of the product in the soil or in a construction constituting the environmental medium to be protected against termites.

The polymer or polymers constituting the core are a function of the substance used that is active against termites. Generally, the polymeric binder, preferably thermofusible, present individually or in the form of a mixture in the matrix of the core, is selected from the group consisting of vinyl and polyolefin polymers and copolymers, acrylic polymers and copolymers, polyamids, polyesters, silicon and insoluble cellulosic derivatives, such as cellulose diacetate and cellulose acetate and polyurethanes.

It is to be noted that to facilitate the release of the active substance from the matrix, the matrix can moreover comprise hydrophilic substances which promote the absorption of water into the matrix.

In the case of formation by extrusion or molding, the core is constituted:

from 1 to 40% by weight, preferably 5 to 25% by weight, of a substance active against termites and from 60 to 99% by weight, preferably 75 to 95% by weight, of polymers and if desired additives such as a porous filler, starch or a plasticizer, and in that, in the case of a sintered embodiment, the core is constituted:

from 1 to 99% by weight, preferably 10 to 70% by weight, of active substance and from 1 to 99% by weight, preferably 30 to 90% by weight, of binder polymer and additives.

In what follows, a first embodiment of a core involves the incorporation of THERMIDOR 80 WG (trademark) (concentrated to 80% in FIPRONIL) in said core.

EXAMPLE 1

The temperature of degradation of FIPRONIL is 196° C. It is therefore necessary not to exceed 180 ° C. as the extrusion temperature. The polymer used is preferably cellulose diacetate such as BIOCETA (trademark) (produced by Mazzucchelli). The BIOCETA is a thermoplastic material which has the characteristic of being biodegradable thanks to the plasticizers which accelerate the degradation by micro-organisms. There is incorporated up to 20% by mass of FIPRONIL in this polymer. To obtain perfect homogeneity of the polymer-FIPRONIL powder mixture, the latter not having the same granulometry, it is necessary to compress the TERMIDOR (trademark) powder with a hydropress under a maximum pressure of 22MPa so as to form tablets of TERMIDOR (trademark) which can then be easily cut into granules. These granules disperse in the polymer upon the passage through the extruder. The extruder used is a single screw polytropic extruder. The screw has a diameter of 30 mm, a length/diameter ratio of 24D and a degassing region. The hopper is of the gravity feed type. There is also used a filter upstream of the extrusion dye, this filter ensuring a counterpressure permitting avoiding the phenomenon of pumping and also ensuring homogenization of the material. It is thus possible to obtain cores of BIOCETA loaded with 10% FIPRONIL. The temperatures of the different heating regions of the extruder (mixture of BIOCETA/FIPRNOIL) for this extrusion are the following:

| | |
|---|---|
| Zone 1 | 155° C. |
| Zone 2 | 165° C. |
| Zone 3 | 180° C. |
| Extrusion dye | 175° C. |

The speed of rotation of the screw varies between 10 and 15 turns per minute.

Analogous results have been attained with another biodegradable polymer of cellulose acid base and starch such as MATER-BI (produced by Novamont). It is characterized by a behavior upon biodegradation similar to that of paper. MATER-BI has a starch content and a content of natural additives greater than or equal to 60%. It comprises synthetic components constituted of polymers of polyvinyl alcohol, non-toxic, capable of interaction with starch. The microstructure of MATER-BI interpenetrates at the molecular level and permits, during the phase of degradation of the starch, the formation of a strongly inflated structure, promoting a more rapid attack of the synthetic phase by micro-organisms.

BIOCETA however is more interesting by reason of its mechanical strength, its modulus of elasticity being about 1400 MPa.

Similarly, there can be cited the use of Biomax which is hydro/biodegradable polyester.

Similarly, other polymers such as polyethylene bloc amide (PEBA), polyethylene and EVA copolymers, such as ethylene vinyl acetate copolymer, namely ELWAX 40 W ™, could be used.

Cellulosic derivatives could also be used because they have a high mechanical strength, high resistance to shock and low weight as well as high absorption of water.

In this first embodiment described above, the core is thus formed directly by extrusion of a mixture of binder polymer and of the substance active against termites. The shaping of such a core can also be obtained by injection or compression from the same mixture. The same is true in the examples that follow.

In a second embodiment of core described in example 2 below, the core is formed by extrusion of the mixture of a binder polymer, preferably extrudable with a pre-mixture constituted by materials active against termites, of a plasticizer and a porous filler such as pyrolyzed silica, permitting the incorporation of a liquid active substance. This embodiment is more particularly used when the active substance has a low melting point, as is the case for example with CHLORPYRIFOS and BIFENTHRINE.

EXAMPLE 2

The active substance used is CHLORPYRIFOS sold under the trademark DURSBAN FE (concentration of 97% active material). CHLORPYRIFOS is present in the form of crystals which become liquid at 40° C. This molecule decomposes at 160° C. The extrusion temperature must not exceed this temperature. The polymer used is BIOCETA as described above. However, to lower the extrusion temperature of BIOCETA, there is used a plastifying agent, such as glycerin. Thus, there is prepared, at a temperature of the order of 50° C. corresponding to the melting temperature of CHLORPYRIFOS, a pre-mixture constituted in weight percent by 50% CHLORPYRIFOS, 35% glycerin and 15% pyrolyzed silica. 20% of this pre-mixture is withdrawn to mix it with 80% of the BIOCETA polymer and there is obtained after extrusion a core comprised of 80% of BIOCETA polymer, 10% of CHLORPYRIFOS, 7% of glycerin and 3% of silica.

In this case, the temperatures of the different heating regions of the extruder are:

| | |
|---|---|
| Zone 1 | 130° C. |
| Zone 2 | 140° C. |
| Zone 3 | 145° C. |
| Extrusion nozzle | 140° C. |

A similar method can be used with BIFENTRINE.

In still another embodiment of the invention, described in example 3 below, the extruded core is formed by a core constituted of at least one polymer having a modulus of elasticity greater than 500 MPa to confer a mechanical strength on the core and a cladding enveloping the core, the cladding being constituted by substances active against termites, a composition soluble in water and preferably biodegradable, such as starch, and a polymer extrudable at low temperature, such as a vinyl ethylene acetate copolymer, the core and cladding being obtained by co-extrusion.

EXAMPLE 3

Starch also absorbs soluble active materials. There can thus be formed a hot mixture of active substances and starch containing between 30 and 70% of starch. This mixture is viscous when hot and can thus be used more easily as a load than the pure active substance which is too liquid. There is obtained, after resolidification, a hard and brittle solid which melts more slowly the higher the starch content. But this mixture can be extruded only at low temperature. The retained polymer is hence ELWAX (vinyl ethylene acetate copolymer). This polymer is not biodegradable and is only slightly hydrophilic. But starch being soluble in water and biodegradable, the core will ultimately have the desired characteristics. The essence of the core is itself pure BIOCETA. It serves uniquely for giving mechanical strength to the core. The cladding of this is thus formed by a mixture of ELWAX/starch/active substance, to impart slow release of the active substance.

Here is an example of a possible composition of the cladding of the core, expressed in weight percent:

25% CHLORPYRIFOS
60% starch
15% ELWAX

Generally speaking, the core described above has a modulus of elasticity from 500 to 4000 MPa and a modulus of flexure of 450 to 3600 MPa.

As mentioned above, the product to destroy termites contains, in addition to the core, an envelope covering the core. This envelope contains, in addition to the active substance, at least one constituent at least partially soluble in the surrounding medium. The active substance of the envelope is released into the surrounding medium at least at the action of ambient moisture of the surrounding medium or a liquid introduced into this medium according to the kinetics shown in the single figure of drawing. By surrounding medium, is meant any emplacement at a site to be protected such as a wall, soil or other material in which the product, which is the object of the invention, can be implanted.

It is to be noted that the envelope is at most ⅓ of the total weight of the product:

The envelope contains:

1 to 98% by weight of a substance active against termites,
1 to 95% by weight of a binder at least partially soluble in a liquid, said binder comprising at least starch and/or a polymer of the core and/or a cellulosic derivative, such as methylcellulose or carboxymethylcellulose,
1 to 50% by weight of a plasticizer such as glycerin,
0 to 60% by weight of starch.

This envelope contains a concentration of active material, relative to the total weight of the active material in said body, comprised within the range 1 to 99% by weight, preferably 25 to 75% by weight. Generally, this envelope is applied by dipping on the surface of the core, this dipping being followed by drying. To do this, it is necessary to prepare an aqueous solution of starch and/or soluble cellulosic derivatives. It has been determined in the course of tests that the starch should not be used alone, because after deposition by dipping and then drying, it has no mechanical strength on the core and would fall in the form of powder at the touch. Conversely, with pure cellulosic derivatives, it is difficult to obtain a mixture both homogeneous and fairly viscous to deposit a sufficient layer on the core: either the solution was too liquid and did not adhere to the core, or it remained very lumpy. Similarly, the absence of plasticizer resulted in the envelope having a tendency to detach from the core. For all these reasons, it was decided to incorporate in the constituent elements of the envelope a glue of the paper glue type. An example of embodiment of the composition of such a glue is given in U.S. Pat. No. 5,087,649. By way of example, the glues used can be glues sold under the mark SADER produced by Atofinley, under the trademark METHYL CL produced by the Henkel Company, or under the mark PERFAX made by the Henkel Company. These glues are constituted principally of carboxymethylcellulose and starch to which are added additives of the ethyl and methylcellulose type or else EVA (ethylene vinyl acetate copolymer) to render the mixture easy to prepare.

Thus, a first example of a constituent mixture of a possible composition of the envelope for products in the final form of rods 28 cm long and 5 mm in diameter, could be the following:

| | |
|---|---|
| Total mass in grams | 1.8–1.6 |
| Mass of TERMIDOR (trademark) in grams | 0.17–0.15 |
| Mass of carboxymethylcellulose in grams | 0.59–0.82 |
| Mass of starch in grams | 0.34–0 |
| Volume of glycerine in ml | 0.55–0.66 |
| Volume of water before dryinq in ml | 3.7–3.9 |

Similarly, to have an envelope containing 0.26 g of glue of the paper glue type, 0.25 g of TERMIDOR, 0.08 g of glycerine, the core in the form of a rod of 5 mm diameter and 28 cm length was dipped in a mixture containing 200 ml water, 10 g glue, 9.5 g TERMIDOR, 2.5 ml glycerine. There can thus be produced an envelope containing up to 80% of TERMIDOR and to deposit about 1.5 g of TERMIDOR on a rod of the mentioned dimensions and this with a single dipping.

It is to be noted that, in general, in the case in which the plasticizer is glycerine, it is necessary to add between 0.1 and 0.4 ml of glycerine per gram of glue to have a correct envelope. Beyond this range, the envelope crumbles or is gluey.

In the case of the use of CHLORPYRIFOS, the composition in weight percentage before drying of the constituent mixture of the envelope is as follows:

| | |
|---|---|
| CHLORPYRIFOS | 7% |
| Starch | 15% |
| Glue | 7% |
| Glycerine by mass | 3% |
| Water | 68% |

With such a mixture, there is deposited about 0.35 gram of CHLORPYRIFOS per dip on a rod 28 cm long and 5 mm in diameter. There can thus be deposited the required quantities with three dippings.

Of course, other examples of envelopes could also be given.

In short, in the case in which it is desired to produce a product to prevent the presence and/or to destroy termites, in the form of a generally elongated solid body having a length of 28 cm and a diameter of 5 mm, the product could have the following composition:

TABLE 1

| | Materials | Mass proportions (%) | Quantities (g) for 28 cm D = 5 mm |
|---|---|---|---|
| Core | BIOCETA | 89.42 | 6.34 |
| | TERMIDOR | 10.58 | 0.75 |
| Envelope | Soluble binder (paper glue) | 44.07 | 0.26 |
| | Glycerine | 13.56 | 0.08 |
| | TERMIDOR | 42.37 | 0.25 |

Generally, the final product is present in the form of a solid elongated body which has either the shape of a rod of a diameter comprised in the range 3 to 10 mm, preferably about 5 mm, and a length comprised in the range 10 to 40 cm, or the form of a continuous filament of a diameter preferably comprised in the range of 3 to 10 mm. The surface of the rod can have a suitable shape to promote exchange with the surrounding medium.

It is to be noted that another technique could be used for depositing the envelope on the core. Here it is a question of the so-called dusting technique. In this case, the envelope is constituted, in addition to the active substance, of a core polymer. There is utilized in this case the adhesive property of the polymer that constitutes the core to deposit, at the output of the extruder, the active substance constituting the envelope. Thus, tests have been carried out with ethylene vinyl acetate copolymer which is adhesive when hot and hence at the end of the extrusion nozzle. It was deposited by dusting on the average 0.085 mg/mm$^2$ of TERMIDOR (trademark) namely 0.375 grams, on a rod of a length of 180 mm in a diameter of 5 mm. In the case of this technique, it is necessary to compress the active substance of the envelope on the core, this compression being carried out by calendaring so as to avoid detachment of the active substance from the core upon touching it. Industrially, this dusting could be carried out by a type of grain silo with a recovery and recycle bin for the undeposited active substance.

This technique could also be replaced by a fluidized bath. In this case, the compressed air is sent to a bin containing TERMIDOR. The core thus passes through a sort of powder cloud formed by the TERMIDOR.

Thanks to such a structure of the rods, the envelope permits, after a short period of induction T0 at most equal to T1/2, diffusing the active material very rapidly over a period of time T1 at most equal to two weeks such that an anti-termite barrier will be effective about the edifice a short time after application of the product. This period T1, corresponding to the time during which the quantity of active material is freed in the surrounding medium by the envelope, will hence vary from several hours to several days as a function particularly of the moisture content in the surrounding medium. Thus, in a surrounding medium constituted 100% of water, the general shape of the degradation curve of the envelope is like that shown in the single figure of drawing, in which the ordinate of the curve corresponds to the variation in weight of the specimen immersed in the medium in the course of time. This specimen was a rod having the following characteristics:

| | |
|---|---|
| core weight + plus envelope: | 1.376 g |
| envelope weight: | 0.0376 g |
| envelope composition: | 75% glue of the paper to glue type |
| | 15% TERMIDOR |
| | 20% glycerine (by mass) |

The core diffuses slowly the rest of the active material over a period T2 at least equal to ten times T1 and permits guaranteeing an anti-termite barrier for five years. Thus, T2, corresponding to the period during which the quantity of active material is freed by the core in the surrounding medium, is generally at least equal to two years and it can be considered that the active substances remain in the soil for more than three years. As termites move underground, at a depth between 0 and 40 cm, the rods are implanted at a height of 20 cm, between 10 and 30 cm depth. To increase the effectiveness of the barrier, it is possible to arrange the rods at 45°. In this case, there are used rods of about 28 cm length. The efficacy of such a product for destroying termites will be better understood when it is realized that termites have the tendency to develop in moist media, the moisture promoting the freeing of the active principal of the active substance of the envelope.

The formation of the product in the form of a rod facilitates its implantation. Thus, it is necessary only to provide holes in the construction or in the ground and to implant the rod in the cavity thus provided to permit protection of the construction. Generally, these rods will be implanted in the ground and/or in the construction at a spacing between them of about 20 cm. Their radius of activity will hence be of the order of 10 cm.

The other preferred embodiment of product in which the product is present in the form of a continuous filament permits avoiding any creation of an unprotected region around the protective region. Thus, in this case, the product is disposed so as completely to surround the region to be protected. There is thus no possibility of passage for the termites.

The product as described above will be packaged in a sufficiently dry atmosphere to prevent any release of active substance before implantation of the product in any position at a site to be protected. Moreover, it is possible to add within the envelope and/or within the core, different additives such as:
  stabilizers,
  accelerators for the degradation of mineral or organic fillers improving hardness, hydrophilic property or hydrophobic property of the product,
  organic or mineral colors,
  repulsive agents protecting domestic animals,
  and all other phytosanitary elements such as fungicides, insecticides . . . which can be administered synergetically with the termicide.

To guarantee release at two times of the active substance, it is preferable, at the time of implantation of the product that destroys termites, in the form of a rod, in the soil or in a predetermined placement of the construction, to moisten by wetting the region adapted to receive this product before or after positioning this product in the emplacement. It is thus guaranteed that the moisture present in said emplacement, will be sufficient to permit the desired rapid release of said active substance of the envelope.

What is claimed is:
1. A termicidal product to prevent the presence of and/or What is claimed is: to destroy termites comprising:
  an elongated solid core formed by extrusion, molding or sintering, said core constituting a solid macroscopic biodegradable matrix, said core having admixed therein at least one binding polymer and at least one substance active against termites releasable over a first period of time (T2), wherein the binding polymer is selected from the group consisting of vinyl and polyolefin polymers and copolymers, acrylic polymers and copolymers, polyamides, polyesters, silicones, polyurethanes and insoluble cellulosic derivates; and
  an elongated solid envelope surrounding said core and having admixed therein at least one substance active against termites, said active substance of said envelope being releasable by contact of said envelope with moisture wherein said envelope and said core form a solid body; wherein said envelope contains:
  from 1 to 98% by weight of said at least one substance active against termites,
  from 1 to 95% by weight of a binder,
  from 1 to 50% by weight of a plasticizer, and
  from 0 to 60% by weight of starch; and
  wherein the active substance of said envelope, when said product is exposed to moisture, is released over a second period of time, said second period of time corresponding at most to T2/10, such that the active substance of the envelope is released at least ten times more rapidly than the active substance of the core,
  said envelope releasing its said active substance over said second period of time so as to eliminate an infestation of termites and said core releasing its said active substance over said first period of time for preventing reinfestation of termites.

2. The termicidal product according to claim 1, wherein the concentration of said at least one substance active against termites is between 25 to 75% by weight.

3. The termicidal product according to claim 1, wherein the envelope is applied to the surface of the core by dipping.

4. The termicidal product according to claim 1, wherein the active substance is selected from the group consisting of phenyl-pyrazole compounds, organophosphores, organochloro compounds, pyrroles and synthetic pyrethrinoids.

5. The termicidal product according to claim 1, wherein the substances active against termites of the envelope and of the core are the same.

6. The termicidal product according to claim 1, wherein the substances active against termites of the envelope and of the core are different.

7. The termicidal product according to claim 1, wherein the core comprises;
  1 to 40% by weight of said substance active against termites, and
  60 to 99% by weight of said binding polymer.

8. The termicidal product according to claim 1, wherein the core is formed by extrusion of a mixture of a polymeric binder, a plasticizer and a porous filler.

9. The termicidal product according to claim 1, wherein the core comprises:
  at least one polymer having a modulus of elasticity greater than 500 MPa to confer mechanical strength on the core, and
  a cladding enveloping said core, said cladding comprising:
  a compound soluble in water and biodegradable, and a polymer extrudable at low temperatures, said core and said cladding being obtained by co-extrusion.

10. The termicidal product according to claim 1, wherein the envelope is at most ⅓ of the total weight of the product.

11. The termicidal product according to claim 1, wherein the elongated body is a rod having a diameter between 3 to 10 mm, and a length between 10 to 40 cm.

12. The termicidal product according to claim 1, wherein the elongated body is a continuous filament having a diameter between 3 to 10 mm.

13. A process for the implantation of the product according to claim 1 for destroying termites in a region at a site to be protected comprising the steps of:

wetting said site with liquid, and positioning said product in said region.

* * * * *